United States Patent
Proulx et al.

(10) Patent No.: US 9,115,998 B2
(45) Date of Patent: Aug. 25, 2015

(54) TRACKING SYSTEM AND METHOD

(75) Inventors: Catherine Proulx, Verdun (CA); Bruno Falardeau, Verdun (CA); Myriam Valin, Laval (CA); Julie Deslongchamps, Brossard (CA)

(73) Assignee: ORTHOSOFT INC., Montreal (CA)

( * ) Notice: Subject to any disclaimer, the term of this patent is extended or adjusted under 35 U.S.C. 154(b) by 0 days.

(21) Appl. No.: 13/056,132

(22) PCT Filed: Jan. 19, 2010

(86) PCT No.: PCT/CA2010/000079
§ 371 (c)(1),
(2), (4) Date: Jan. 27, 2011

(87) PCT Pub. No.: WO2011/088541
PCT Pub. Date: Jul. 28, 2011

(65) Prior Publication Data
US 2012/0277634 A1    Nov. 1, 2012

(51) Int. Cl.
*A61B 19/00* (2006.01)
*G01C 25/00* (2006.01)
*A61B 17/00* (2006.01)

(52) U.S. Cl.
CPC .......... *G01C 25/005* (2013.01); *A61B 19/5244* (2013.01); *A61B 2017/00725* (2013.01); *A61B 2019/5248* (2013.01)

(58) Field of Classification Search
USPC ............... 600/424, 426, 587, 595; 702/92–95
See application file for complete search history.

(56) References Cited

U.S. PATENT DOCUMENTS

| | | | |
|---|---|---|---|
| 5,971,976 A | 10/1999 | Wang et al. | |
| 6,122,538 A | 9/2000 | Sliwa, Jr. et al. | |
| 6,490,467 B1 * | 12/2002 | Bucholz et al. | 600/407 |
| 6,786,877 B2 | 9/2004 | Foxlin | |
| 7,065,393 B2 * | 6/2006 | Sati et al. | 600/407 |
| 7,277,594 B2 * | 10/2007 | Hofstetter et al. | 382/275 |
| 7,594,933 B2 * | 9/2009 | Kammerzell et al. | 623/22.15 |
| 8,057,479 B2 * | 11/2011 | Stone | 606/91 |
| 8,057,482 B2 * | 11/2011 | Stone et al. | 606/102 |
| 8,118,815 B2 * | 2/2012 | van der Walt | 606/102 |
| 8,265,790 B2 * | 9/2012 | Amiot et al. | 700/245 |
| 2002/0103610 A1 * | 8/2002 | Bachmann et al. | 702/94 |
| 2004/0039396 A1 * | 2/2004 | Couture et al. | 606/87 |
| 2004/0243148 A1 | 12/2004 | Wasiliewski | |
| 2005/0113646 A1 * | 5/2005 | Sotos et al. | 600/300 |
| 2006/0015018 A1 * | 1/2006 | Jutras et al. | 600/301 |
| 2007/0032723 A1 | 2/2007 | Glossop | |
| 2007/0032748 A1 | 2/2007 | McNeil et al. | |
| 2007/0100346 A1 * | 5/2007 | Wyss et al. | 606/87 |

(Continued)

FOREIGN PATENT DOCUMENTS

| | | |
|---|---|---|
| DE | 202006010728 | 9/2006 |
| WO | 2009117832 | 10/2009 |

*Primary Examiner* — Sean Dougherty
(74) *Attorney, Agent, or Firm* — Norton Rose Fulbright Canada LLP (57) ABSTRACT

A tracking system is provided for tracking objects. A first and a second trackable member each have an inertial sensor unit producing at least orientation-based data. A processing unit receives the orientation-based data from the trackable members. The processing unit has an orientation calculator calculating an orientation of the second trackable member with respect to the first trackable member from the orientation-based data of the trackable members, whereby the processing unit calculates an orientation of the objects. A method for tracking objects is also provided.

21 Claims, 7 Drawing Sheets

(56) References Cited

U.S. PATENT DOCUMENTS

| | | |
|---|---|---|
| 2007/0287901 A1 | 12/2007 | Strommer et al. |
| 2007/0287911 A1 | 12/2007 | Haid et al. |
| 2008/0039868 A1 | 2/2008 | Tuemmler et al. |
| 2008/0051910 A1 | 2/2008 | Kammerzell et al. |
| 2008/0065084 A1* | 3/2008 | Couture et al. ............... 606/86 |
| 2009/0138019 A1* | 5/2009 | Wasielewski ............... 606/87 |
| 2009/0187120 A1* | 7/2009 | Nycz ............................ 600/587 |
| 2009/0221937 A1 | 9/2009 | Smith |
| 2009/0247863 A1* | 10/2009 | Proulx et al. ............... 600/426 |
| 2009/0248044 A1* | 10/2009 | Amiot et al. ............... 606/130 |
| 2009/0300811 A1* | 12/2009 | Lundahl ............................ 2/15 |
| 2010/0016705 A1* | 1/2010 | Stone ............................ 600/407 |
| 2010/0063508 A1* | 3/2010 | Borja et al. ..................... 606/88 |
| 2010/0064216 A1* | 3/2010 | Borja et al. ..................... 715/705 |
| 2011/0031735 A1* | 2/2011 | Gerigk et al. ................... 283/70 |
| 2011/0196377 A1* | 8/2011 | Hodorek et al. ............... 606/87 |
| 2011/0275957 A1* | 11/2011 | Bhandari ...................... 600/595 |
| 2012/0053594 A1* | 3/2012 | Pelletier et al. ............... 606/102 |
| 2012/0074876 A1* | 3/2012 | Redler ............................ 318/41 |
| 2012/0277634 A1* | 11/2012 | Proulx et al. ................. 600/595 |

\* cited by examiner

TRACKING SYSTEM AND METHOD

CROSS-REFERENCE TO REPLATED APPLICATION

The present application is a U.S. national-phase entry of International Application No. PCT/CA2010/000079, bearing an International Filing Date of Jan. 19, 2010.

FIELD OF THE APPLICATION

The present application relates to tracking systems such as those used in computer-assisted surgery systems and, more particularly, to instrumentation used for the tracking of surgical tools during computer-assisted surgery and to a method for calibrating inertial sensors.

BACKGROUND OF THE ART

Tracking of surgical instruments or tools is an integral part of computer-assisted surgery (hereinafter CAS). The tools are tracked for position and/or orientation in such a way that information pertaining to bodily parts is obtained. The information is then used in various interventions (e.g., orthopedic surgery, neurological surgery) with respect to the body, such as bone alterations, implant positioning, incisions and the like during surgery.

The tracking systems may use different technologies, such as mechanical, acoustical, magnetic, optical and RF tracking. Depending on the technology used, different types of trackable members are fixed, permanently or temporarily, to the item that needs to be tracked. For instance, during Total Knee Replacement (TKR) surgery, trackable members are fixed to the limbs and to the different surgical instruments, and these trackable members are tracked by the tracking system. The CAS system calculates position and orientation data associated with the tracking, and the information displayed by the computer is used by the surgeon to visualize the position of the instrument(s) being manipulated with respect to the limbs, or in numerical values.

Two types of tracking systems are commonly used. Active tracking systems provide a transmitter as a trackable member on the tool to be tracked, which transmitter emits signals to be received by a processor of the CAS system, which will calculate the position and/or orientation of the tool as a function of the signals received. The transmitters of the active tracking systems are powered, for instance by being wired to the CAS system or by being provided with an independent power source, so as to emit signals.

Passive tracking systems do not provide active transmitters on the tools as trackable members. The CAS system associated with passive tracking has an optical sensor apparatus provided to visually detect optical elements on the tools. The optical elements are passive, whereby no power source is associated therewith.

In order to obtain values for position and/or orientation, the optical elements must be in the line of sight of the optical sensor apparatus. Accordingly, with passive tracking systems, surgery takes place in a given orientation as a function of the required visibility between the optical sensor apparatus and the optical elements.

The trackable members currently used, whether active or passive, have a noticeable size depending on the technology used. For an electromagnetic system, a casing is wired to the CAS system and is secured to the instrument or to the patient. For an optical system, a trackable member generally comprises at least three optical elements. For instance, the optical elements are light sources wired to the CAS system and forming a scalene triangle. The light sources can be individually fixed or assembled on a base.

As an alternative, passive reflector spheres or patches can be used instead of light sources, and a light source is used to illuminate them (in the infrared spectrum).

Some factors must be considered when selecting a type of tracking system: the presence of wires in sterile zones for active trackable members; a line of sight required for navigation when using optical tracking; the size of the trackable members in order to deliver the required precision during surgery; the necessity for the surgeon to visualize a computer screen for intraoperative alignment information; the necessity for the surgeon to digitize landmarks on bones in order to build coordinate systems; the difficulty in integrating current optical, electromagnetic or radio-frequency sensors in disposable instruments (such as cutting guides) because of their volume.

SUMMARY OF THE APPLICATION

It is therefore an aim of the present application to provide a novel trackable member and tracking system.

It is a further aim of the present application that the tracking system be used in computer-assisted surgery.

Therefore, in accordance with the present application, there is provided a computer-assisted surgery system for tracking an instrument and a bone during surgery, comprising: a first trackable member having a first inertial sensor unit producing at least orientation-based data, the first inertial sensor unit being an accelerometer-based unit adapted to be affixed to the bone, to produce orientation data for two degrees of freedom of orientation; and a second trackable member having a second inertial sensor unit producing at least orientation-based data, the second inertial sensor unit being an accelerometer-based unit adapted to be affixed to the bone, to produce orientation data for two degrees of freedom of orientation; and a processing unit for receiving the orientation-based data from the trackable members, the processing unit comprising: an orientation calculator calculating an orientation of the second trackable member with respect to the first trackable member from the orientation-based data of the trackable members, the orientation calculator determining angular rates of change of the first inertial sensor unit and the second inertial sensor unit after the bone is moved in space, and a calibration calculator for calibrating an orientation of the bone with reference to the first inertial sensor unit by using the determined angular rates of change to determine a third degree of freedom of orientation of the first inertial sensor unit, whereby the bone is trackable in three degrees of freedom of orientation.

Further in accordance with the present application, the first trackable member and the second trackable member produce position-based data, and the processing unit stores geometrical data relating at least one of the trackable members to the bone and another of the trackable members to the instrument, whereby the orientation calculator calculates a position and orientation of the instrument with respect to the bone.

Still further in accordance with the present application, the processing unit is physically part of the second trackable member.

Still further in accordance with the present application, the second trackable member has a user interface to display the orientation of the second trackable member with respect to the first trackable member.

Still further in accordance with the present application, at least one of the trackable members has a confirmation indicator receiving signals from the processing unit to visually display a confirmation of command from the at least one trackable member.

Still further in accordance with the present application, the first trackable member and the second trackable member are arbitrarily placed on the bone, and the processing unit determines a preferred virtual orientation from the orientation of the second trackable member with respect to the first trackable member, the orientation calculator determining the angular rates of change from the preferred virtual orientation.

In accordance with another embodiment of the present application, there is provided a method for tracking three degrees of freedom of orientation of an object, the method comprising: receiving orientation data for two degrees of freedom of orientation from an accelerometer-based reference tracking member affixed to the object; receiving orientation data for two degrees of freedom of orientation from an accelerometer-based calibration tracking member affixed to the object; determining angular rates of change of the reference tracking member and of the calibration tracking member while the object is moved in space; and calibrating an orientation of the object with reference to the reference tracking member by using the determined angular rates of change to determine a third degree of freedom of orientation of the reference tracking member; whereby the object is trackable in three degrees of freedom of orientation.

Still further in accordance with the other embodiment of the present application, receiving orientation data comprises receiving orientation data from the reference and calibration tracking members affixed to a bone.

Still further in accordance with the other embodiment of the present application, determining angular rates of change of the reference tracking member and of the calibration tracking member comprises displaying data associated to an angular rate of change, for guiding an operator in moving the object.

Still further in accordance with the other embodiment of the present application, the method is performed with a bone model or a cadaver.

Still further in accordance with the other embodiment of the present application, a tracking of the object is displayed in three degrees of freedom of orientation on an interface after the calibrating.

Still further in accordance with the other embodiment of the present application, receiving orientation data from the reference tracking member comprises first placing the reference tracking member in alignment with object axes.

Still further in accordance with the other embodiment of the present application, receiving orientation data from the reference tracking member comprises randomly placing the reference tracking member on the object, and determining a preferred orientation of the reference tracking member with respect to the object, and further wherein determining angular rates of change comprises determining angular rates of change relative to the preferred orientation of the reference tracking member.

In accordance with yet another embodiment of the present application, there is provided a system for tracking three degrees of freedom of an orientation of an object, the system comprising: an accelerometer-based reference tracking member adapted to be affixed to the object, the reference tracking member producing orientation data for two degrees of freedom of orientation; an accelerometer-based calibration tracking member adapted to be affixed to the object, the calibration tracking member producing orientation data for two degrees of freedom of orientation; a processing unit for receiving the orientation data from the reference tracking member and the calibration tracking member, the processing unit comprising: an orientation calculator for determining angular rates of change of the reference tracking member and the calibration tracking member after the object is moved in space; and a calibration calculator for calibrating an orientation of the object with reference to the reference tracking member by using the determined angular rates of change to determine a third degree of freedom of orientation of the reference tracking member; whereby the object is trackable in three degrees of freedom of orientation.

Further in accordance with the yet other embodiment of the present application, the system is a computer-assisted surgery system, the object is a bone and the reference tracking member and the calibration tracking member are affixed to the bone.

Still further in accordance with the yet other embodiment of the present application, a user interface for displaying data is associated with an angular rate of change about the axis of one of the two degrees of freedom of orientation of the reference tracking member, for guiding an operator in moving the object.

Still further in accordance with the yet other embodiment of the present application, the user interface displays a tracking of the object in three degrees of freedom of orientation on an interface after the calibrating.

Still further in accordance with the yet other embodiment of the present application, the reference tracking member and the calibration tracking member are randomly placed on the object, and the processing unit determines a preferred orientation of the reference tracking member with respect to the object, the orientation calculator further determining the angular rates of change from the preferred orientation.

DESCRIPTION OF THE EXEMPLARY EMBODIMENTS

Figure 1:
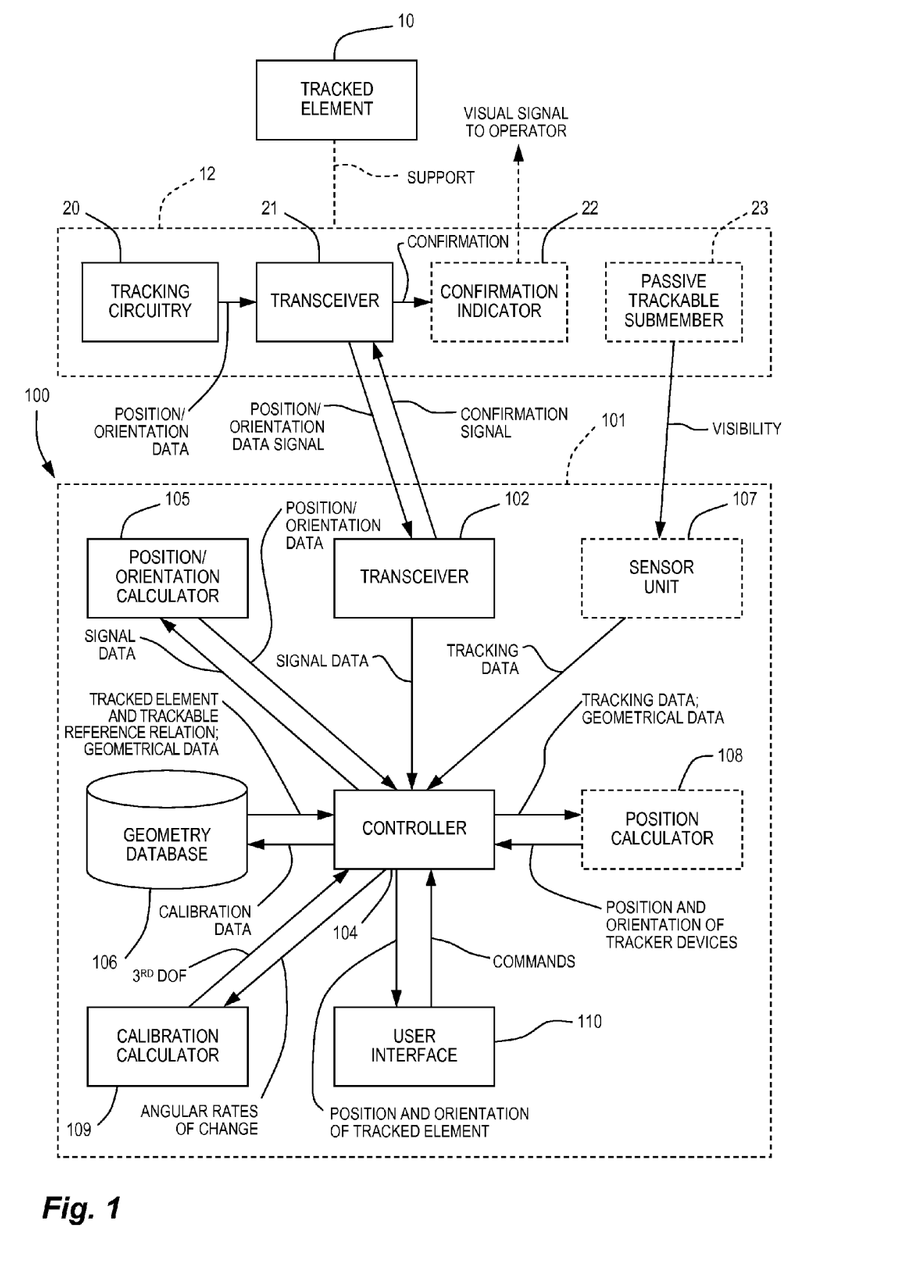
FIG. 1 is a block diagram of a tracking system in accordance with an embodiment of the present application.

Referring to FIG. 1, a MEMS (micro-electro-mechanical system) trackable member in accordance with an embodiment of the present application is generally shown at 12 as being fixed to a tracked element 10, such as a surgical tool, or a bodily element (e.g., bone).

The MEMS trackable member 12 is used in a tracking system (such as a CAS tracking system) and comprises tracking circuitry 20 (i.e., inertial sensor unit), a transmitter 21 (or like communication circuitry, such as a wireless transmitter, a transceiver or the like), and optional confirmation indicator 22 and passive trackable submember 23. Reference to a transmitter will include a transceiver hereinafter, unless stated otherwise.

In an embodiment of the present disclosure, the tracking circuitry may be 6-degree-of-freedom (hereinafter DOF) micro-circuitry. The tracking circuitry 20 outputs data pertaining to the position and orientation of the trackable member 12.

Examples of suitable devices used as tracking circuitry 20 are the capacitive accelerometer sensor (CAPAS), electrolytic tilt sensors and the tri-axis sensor (TAS), amongst other possibilities. The CAPAS provides a 2-axis measurement of the acceleration (e.g., g force) of the tracked element 10 by being fixed thereto. In one embodiment, the physical size of the CAPAS is 7.4 mm by 7.0 mm by 3.5 mm.

A method and system are described hereinafter for the calibration of accelerometer-based tracking circuitry 20 for the accelerometer-based tracking circuitry 20 to provide 3 DOFs of orientation. In some applications, the tracking of 3 DOFs in orientation is sufficient—there is no need for the tracking circuitry 20 to be configured to provide more than the 3 DOFs, or to be connected to a passive trackable member providing the DOFs in position.

In the active state of the CAPAS, variations of the acceleration are reflective of a modification in the orientation of the CAPAS. The output of the CAPAS is a 2-axis relative angular value (or 3-axis if the CAPAS is calibrated). Therefore, the calibrated tracking circuitry 20 or the tracking circuitry 20 having two CAPAS in the aforementioned configuration provide real-time orientation data for the tracking circuitry 20, and thus for the tracked element 10.

In another embodiment, a trackable submember 23 may be provided as part of the trackable member 12, in order to provide position data related to the trackable member 12. Therefore, the orientation data output by the tracking circuitry 20 is combined with the position data obtained from the tracking of the trackable submember 23 to provide spatial position and orientation of the tracked element 10. For the trackable submember 23, known technologies such as ultrasound, optical elements and RF emitters can be used. In one embodiment, a retroreflective element (e.g., sphere, geometrical patch) is used. It is pointed out that a single trackable submember 23 (e.g., one sphere) is required as the trackable submember 23 is used to obtain position data. However, more than one trackable submember 23 can be used to increase the precision of the position data, or to increase the visibility of the trackable members 23, in the case of optical tracking. Therefore, with the use of CAPAS as tracking circuitry 20 with a single trackable submember 23, the trackable member 12 provides 6-DOF position and orientation in a compact device.

In another embodiment, a tri-axis accelerometer is used to provide position data for the trackable submember 23. By integrating the linear acceleration over time, the displacement from a known initial position can be computed to provide the current position of the submember 23.

As an alternative to CAPAS for the tracking circuitry 20, TAS provides position and orientation data. TAS consists of three gyroscopes and three accelerometers embedded in micro-circuitry. As an example, the physical size of an available TAS is 23 mm by 32 mm by 5 mm. Therefore, using one of these TAS will provide position and orientation data as is the case with a combination of a pair of CAPAS and a trackable submember 23, but is larger than the latter combination.

The transmitter 21 is connected to the tracking circuitry 20 so as to transmit the tracking data of the tracking circuitry 20 to the processing system of the CAS system. The transmission of data may be wireless, or through wired connection. The technology used for the transmitter 21 may be selected to operate in a surgical environment, such as RF. As an example, Bluetooth™, IEEE-802.15.4 based protocol, Zigbee™ or Wi-Fi transmitters are considered for their wide availability and allow the integration of the trackable member 12 to surgical instruments. The trackable member can be manufactured as a single disposable unit, possibly integrated to implant instrumentation (e.g. a disposable, self-trackable cutting guide for TKR). As an alternative embodiment, sensors can be configured to communicate necessary information between themselves.

Another feature considered for the trackable member 12 is the confirmation indicator 22 that provides data to the operator or surgeon. For instance, indications about a suitable position/orientation of the surgical tool may be provided directly on the tool, so as to facilitate the procedure for the surgeon/operator handling the tool. The confirmation indicator 22 is circuitry with on/off LEDs (e.g., red and green LEDs) or another suitable form of compact electronic display responsive to signals or commands received from the CAS system. In the embodiment in which the trackable device 12 uses a confirmation indicator 22, the transmitter 21 is a transceiver that receives signals from the processing system of the CAS system. The confirmation indicator 22 is connected to the circuitry of the transceiver to receive signals and convert them to the visual signal provided to the operator/surgeon.

Another embodiment of the confirmation indicator 22 involves a series of LEDs or another suitable form of compact electronic display that would be turned on according to the position and orientation of the instrument upon which the trackable member 12 is fixed. This would allow communication of alignment/position information of the various surgical instruments as the surgeon/operator is manipulating them, in order to free the surgeon from having to look at the computer screen for equivalent information.

Amongst the surgical tools being used as tracked elements 10 are registration pointers, cutting blocks, drills, rasps, writing sticks and the like.

Any suitable types of calibration can also be used with the trackable member 12. For instance, a method is described hereinafter for calibrating an orientation of the tracked element 10 with reference to FIG. 5.

Still referring to FIG. 1, a tracking system incorporating the trackable member 12 is generally illustrated at 100, and is used with one or more of the trackable member 12. The tracking system may be a computer-assisted surgery system (CAS system), and has a processing unit 101, which typically comprises a computer having a processor. A receiver 102 is provided in the processing unit 101 so as to receive the position/orientation data signal from the trackable member 12. In the embodiment in which the trackable member 12 has a confirmation indicator 22, the receiver 102 is a transceiver sending confirmation signals to the trackable member 12.

A controller 104 is connected to the receiver 102. Therefore, the controller 104 receives the signal data from the receiver 102.

A position/orientation calculator 105 is used to convert the signal data received from the receiver 102 into position/orientation data for the trackable member 12. More specifically, if the tracking circuitry 20 is a combination of CAPAS or a calibrated CAPAS, the signal data will be converted to an orientation of the trackable member 12. If the tracking circuitry 20 is a TAS, the signal data will be converted to a position and an orientation of the trackable member 12.

A geometry database 106 is provided so as to store the calibration data, and other intraoperative data such as bone models defined using digitization instruments, for given CAS applications, axes and coordinate systems of objects. The calibration data is therefore a relation between the tracked element 10 and the trackable member 12, when position data is required for the application. In the embodiment in which a trackable submember 23 is used, the calibration data comprises geometrical data relating the trackable submember 23 to the tracked element 10.

Therefore, in an application requiring position data, the controller 104 receives the position/orientation data from the position/orientation calculator 105, and calculates position/orientation of the tracked element 10 using the relation data provided by the database 106. Accordingly, the controller 104 outputs position/orientation data to the user interface 110.

The processing unit 101 optionally has a sensor unit 107 (e.g., optical sensor apparatus) provided in order to track the trackable submember 23 of the trackable member 12, in the embodiment in which the trackable submember 23 is used in combination with a pair of CAPAS, or a calibrated CAPAS. Typically, the sensor unit 107 involves a pair of sensors (e.g., Navitrack™).

A position calculator 108 may be provided in association with the controller 104. The position calculator 108 receives the tracking data from the controller 104, which tracking data is obtained from the tracking by the sensor unit 107. With the geometrical data provided by the database 106, the position calculator 108 calculates the position of the tracked element 10.

The position of the tracked element 10 is sent to the controller 104 and is combined with the orientation of the tracked element 10, whereby the controller 104 produces the position and orientation of the tracked element 10.

The tracking system 100 may be provided with a calibration calculator 109. The calibration calculator 109 is used with a pair of rigidly-fixed 2 DOF orientation trackable members 12 (e.g., CAPAS) as illustrated in FIGS. 3 and 4, and calibrates one of the trackable members 12 such that a third DOF in orientation relative to the first trackable member is known and trackable.

This information is sent to the user interface 110, such that the user of the system 100 obtains information pertaining to the position and orientation of the tracked element 10 in the various forms known to computer-assisted surgery (e.g., visual representation, numerical values such as angles, distances, etc.). It is pointed out that the database 106 may as well be part of the controller 104.

Figure 2:
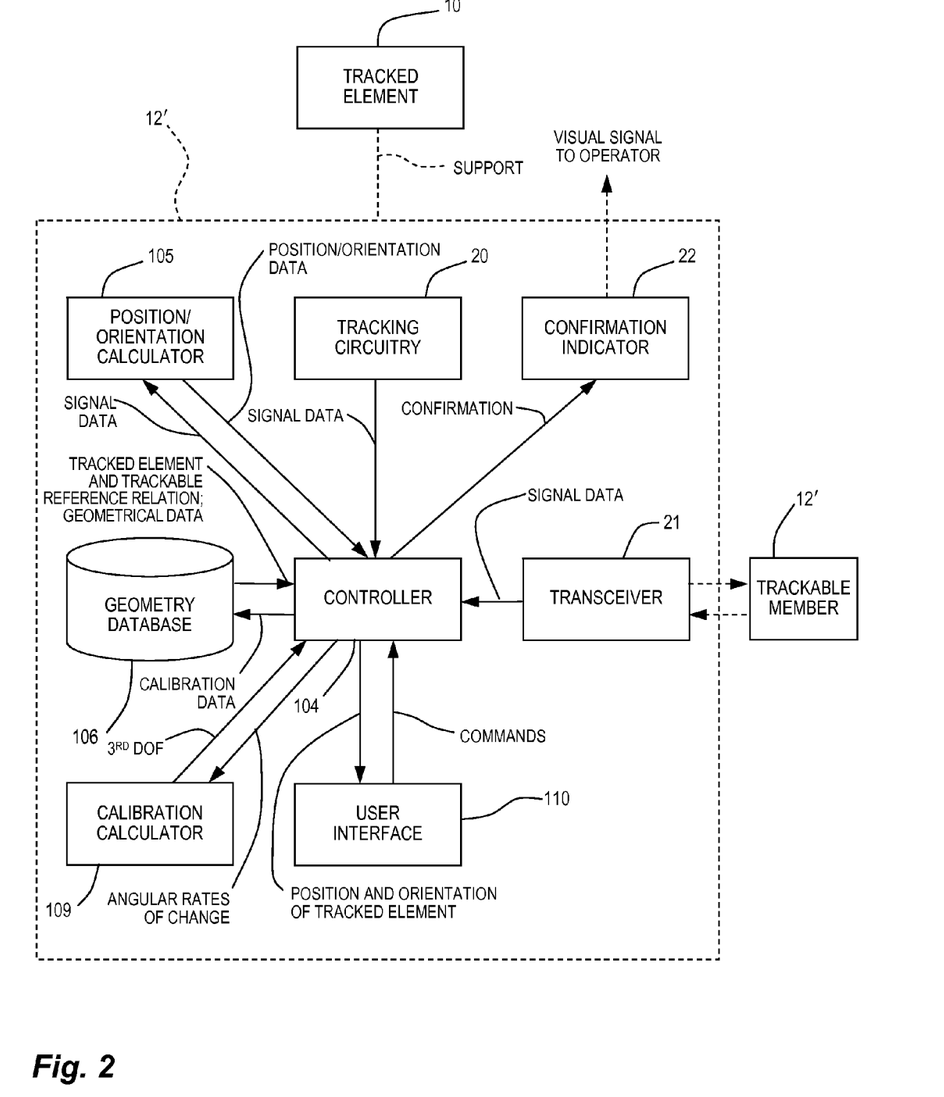
FIG. 2 is a block diagram of a self-enclosed tracking system in accordance with another embodiment of the present application.

Referring to FIG. 2, there is illustrated at 12' an embodiment of the trackable member in which a self-enclosed processing unit is connected to the tracked element 10. The trackable member 12' has the tracking circuitry 20, transceiver 21 and the confirmation indicator 22 described above for the trackable member 12, but also the controller 104, the position/orientation calculator 105, the geometry database 106, the calibration calculator 109 and the user interface 110, all in a compact self-enclosed casing secured directly to the tracked element 10. Accordingly, the transceiver 21 is used to share information with other trackable members 12' used concurrently during the surgical procedure.

Figure 3:
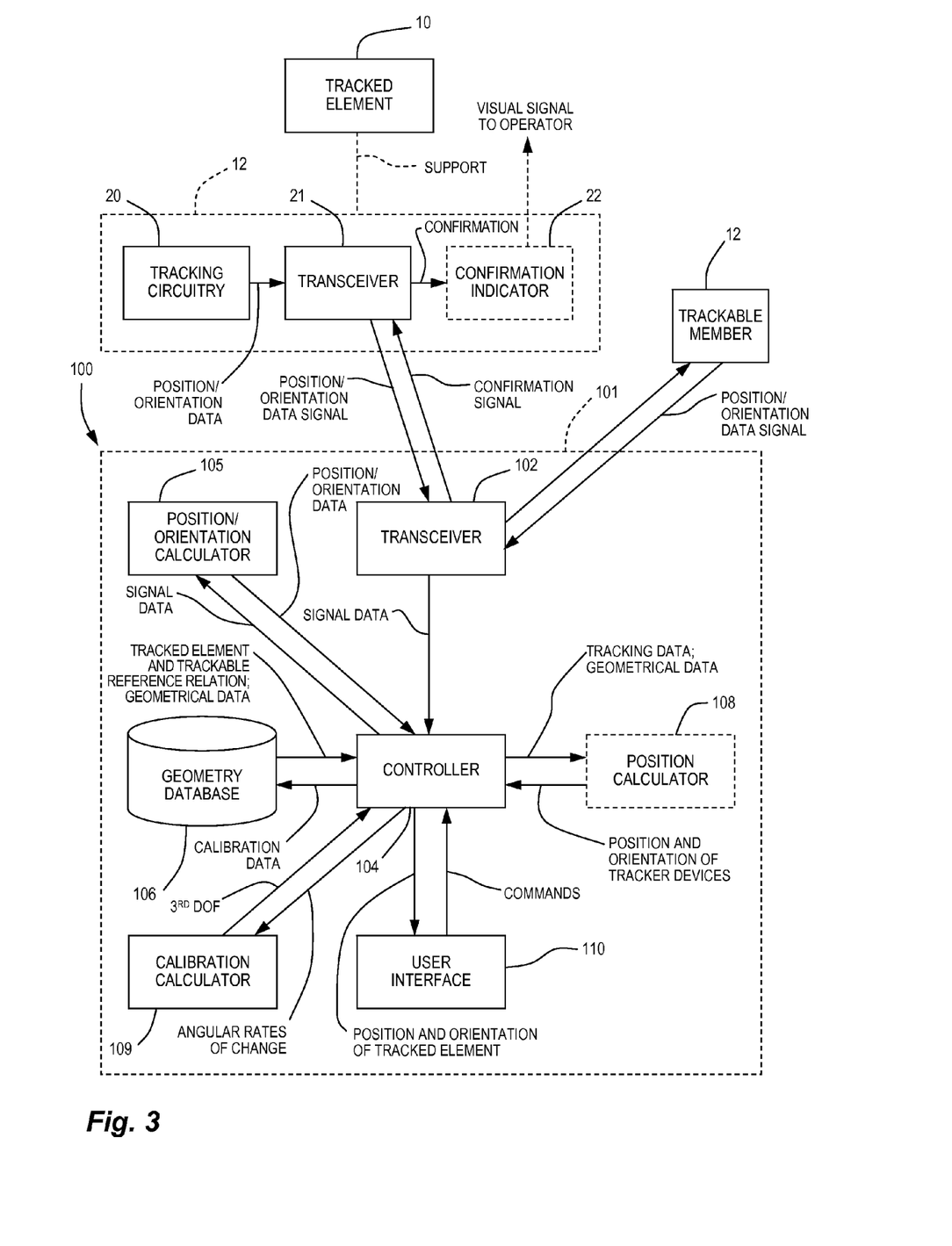
FIG. 3 is a block diagram of a tracking system in accordance with another embodiment of the present application, tracking a pair of trackable members.
Figure 4:
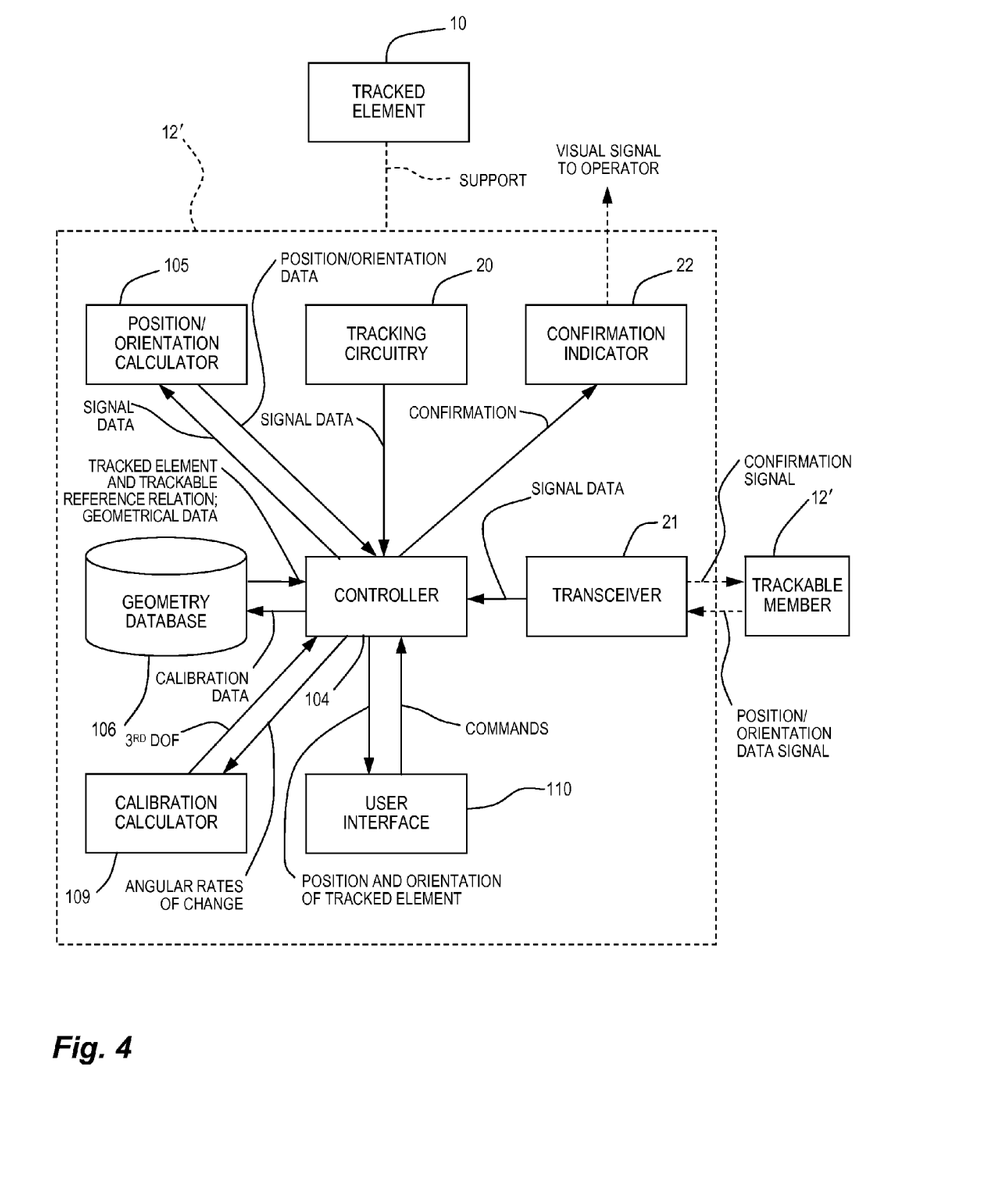
FIG. 4 is a block diagram of a self-enclosed tracking system in accordance with another embodiment of the present application, as used with a trackable member.

In the embodiments of FIGS. 3 and 4, at least two trackable members 12/12' are used in combination, with a first one of the trackable members 12/12' being secured to a bone or other bodily part, while a second one of the trackable members 12/12' is mounted to a tool/instrument, or to the bone for calibration. Therefore, any displacement of the bone is captured by the tracking circuitry 20 of its trackable member 12/12', which information is transmitted to the trackable member 12' on the tool/instrument. The tracking data is shared between the trackable members 12/12' such that the information provided on the user interface 110 represents the relative displacements between the bone and the tool/instrument.

In some instances, only the orientation (e.g., axes) between the bone and the instrument is required. In such a case, the tracking circuitry 21 of the trackable members 12/12' conveniently uses accelerometers.

Now that various systems are described, there is shown a method for calibrating the accelerometer-based tracking circuitry 20 for tracking 3 DOFs in orientation. Firstly, Cartesian coordinates must be converted to tilt angles.

Converting Cartesian Coordinates to Tilt Angles

3-DOF orientation R in space is defined in Cartesian coordinates:

$$R = \begin{bmatrix} x_1 & y_1 & z_1 \\ x_2 & y_2 & z_2 \\ x_3 & y_3 & z_3 \end{bmatrix}$$

where the axes of the oriented point are given by:

$$\vec{x} = (x_1, x_2, x_3)$$

$$\vec{y} = (y_1, y_2, y_3)$$

$$\vec{z} = (z_1, z_2, z_3)$$

Assuming that the world coordinate system has its gravity vector along $-\vec{z}$, (i.e., $\vec{z}$ points toward the sky), and that the ground is on the xy plane, the x angle ($\phi$) and z angle ($\theta$) are defined as follows:

($\phi$)=Angle between $\vec{x}$ and its projection on the ground (positive when $\vec{x}$ points up)

$$\phi = a\sin(x_3) \qquad (1)$$

and:

($\theta$)=Angle between $\vec{z}$ and its projection on the ground (positive when $\vec{z}$ points up)

$$= a\sin(z_3) \qquad (2)$$

A third angle, $\zeta$ is introduced and corresponds to the angle between $\vec{y}$ and its projection on the ground, and also returned by three-axis accelerometers $\zeta$=Angle between $\vec{y}$ and its projection on the ground (positive when $\vec{y}$ points up)

$$= \pm a\cos\sqrt{y_1^2 + y_2^2}$$

$$= a\sin(y_3) \qquad (3)$$

This angle is not sufficient to retrieve the three DOFs of the orientation, since $\vec{y}$ is always perpendicular to the other two vectors. From the properties of the rotation matrix, by which the magnitude of every row and column of an orthogonal matrix is 1, the following identity is set:

$$1 = \sin(\phi)^2 + \sin(f)^2 + \sin(\zeta)^2 \qquad (4)$$

The sign of $\zeta$ will be used to discriminate between symmetrical solutions.

Together, ($\phi$), ($\theta$), and $\zeta$ are called the tilt angles, and form a tilt attitude.

The rotation of a body about the gravity vector, called the yaw (ψ) is defined as follows:

ψ=Angle between $\vec{z}$ projected on the ground and the world's y axis $$= \pm a\cos\left(\frac{z_2}{\sqrt{z_1^2+z_2^2}}\right) \quad (5)$$

$$= \pm a\cos\left(\frac{z_2}{\sqrt{1-z_3^2}}\right)$$

Figure 5:
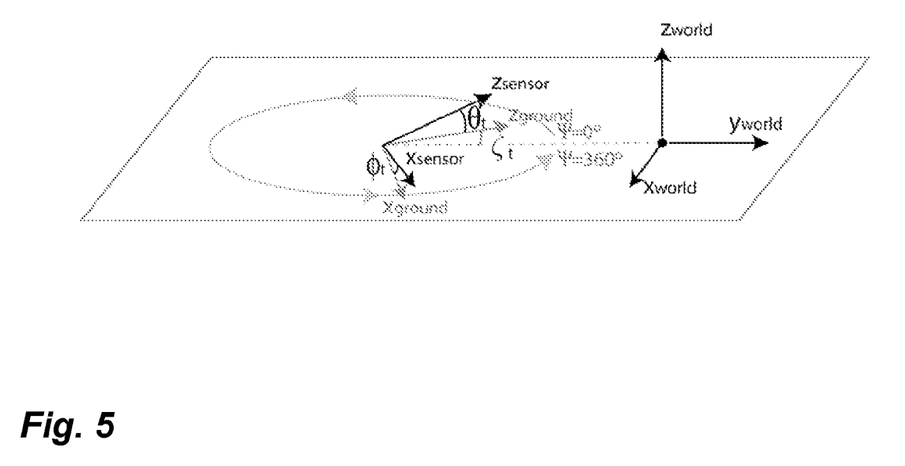
FIG. 5 is a schematic representation of tilt angles and yaw of a sensor in a world coordinate system.

In addition, (ψ) is defined as an angle between 0° and 360°, as illustrated in FIG. 5.

Converting Tilt Angles and Yaw to Cartesian

For the reverse transformation, $\vec{x}$, $\vec{y}$ and $\vec{z}$ must be retrieved from (ϕ), (θ), ζ and (ψ).

From equations (1), (2) and (3), it is known that:

$$x_3 = \sin(\phi) \quad (6)$$

$$y_3 = \sin(\zeta) \quad (7)$$

$$z_3 = \sin(\theta) \quad (8)$$

From equation (5), it is found that:

$$z_2 = \cos(\psi)\sqrt{1-z_3^2} \quad (9)$$
$$= \cos(\psi)\sqrt{1-\sin(\theta)^2}$$
$$= \cos(\psi)\cos(\theta)$$

Since $\vec{z}$ is a unit vector:

$$z_1 = \pm\sqrt{1-z_2^2-z_3^2}$$
$$= \pm\sqrt{1-\cos(\psi)^2\cos(\theta)^2-\sin(\theta)^2}$$
$$= \pm\sqrt{\cos(\theta)^2-\cos(\psi)^2\cos(\theta)^2}$$
$$= \pm\cos(\theta)\sqrt{1-\cos(\psi)^2}$$
$$= \pm\cos\theta\sin\psi$$

The definition of the yaw can be used to establish the sign of $z_1$, since a negative value of $z_1$ is expected when (ψ)<180°.

$$z_1 = -\cos\theta\sin\psi \quad (10)$$

$\vec{x}$ $\vec{z}$ and are perpendicular, and $\vec{x}$ is a unit vector, so:

$$\vec{x}\cdot\vec{z} = x_1 z_1 + x_2 z_2 + x_3 z_3 = 0 \quad (11)$$

$$x_1^2 + x_2^2 + x_3^2 = 1 \quad (12)$$

The following is thus set:

$$x_1 = \frac{-x_3 z_3 - x_2 z_2}{z_1} \quad (13)$$

$$x_1^2 = \frac{x_3^2 z_3^2 + 2x_2 x_3 z_2 z_3 + x_2^2 z_2^2}{z_1^2}$$

By replacing $x_1^2$ by its equivalent from equation (12) and rearranging the terms, the following quadratic equation is obtained in $x_2$:

$$\left(\frac{z_2^2}{z_1^2}+1\right)x_2^2 + \left(\frac{2x_3 z_2 z_3}{z_1^2}\right)x_2 + \left(\frac{x_3^2 z_3^2}{z_1^2}+x_3^2-1\right) = 0 \quad (14)$$

By solving this quadratic for $x_2$, and then $x_1$, two solutions can be formed for $\vec{x}$. These two solutions are differentiated by computing $\vec{y}=\vec{z}\times\vec{x}$. Only one of the possible solutions for $\vec{y}$ will be pointing in the expected direction, defined by the sign of ζ. A solution is thus obtained for R based on the tilt angles and the yaw.

Navigation of a Visual Sensor Relative to a Reference

To track the orientation, in terms of tilt angles, of a point in space, for which the relative orientation to a sensor is known, the following is set forth.

Using the tilt angles of a sensor S and the relative orientation of S relative to the virtual sensor T, ($T_{inS}$), the tilt angles of T are retrieved as follows:

$$T_{inS} = \begin{bmatrix} a & d & g \\ b & e & h \\ c & f & j \end{bmatrix}$$

For any position of T and S:

$$T_{inWorld} = S_{inWorld} \cdot T_{inS} \quad (15)$$

From this, it is known that:

$$\vec{z_{t_{inWorld}}} = S_{inWorld} \cdot T_{inS} \cdot \begin{bmatrix} 0 \\ 0 \\ 1 \end{bmatrix} \quad (16)$$

$$= \begin{bmatrix} x_{s_1} & y_{s_1} & z_{s_1} \\ x_{s_2} & y_{s_2} & z_{s_2} \\ x_{s_3} & y_{s_3} & z_{s_3} \end{bmatrix} \cdot \begin{bmatrix} a & d & g \\ b & e & h \\ c & f & j \end{bmatrix} \cdot \begin{bmatrix} 0 \\ 0 \\ 1 \end{bmatrix}$$

$$= \begin{bmatrix} x_{s_1}g + y_{s_1}h + z_{s_1}j \\ x_{s_2}g + y_{s_2}h + z_{s_2}j \\ x_{s_3}g + y_{s_3}h + z_{s_3}j \end{bmatrix}$$

Similarly, $$\vec{x_{t_{inWorld}}} = \begin{bmatrix} x_{s_1}a + y_{s_1}b + z_{s_1}c \\ x_{s_2}a + y_{s_2}b + z_{s_2}c \\ x_{s_3}a + y_{s_3}b + z_{s_3}c \end{bmatrix} \text{ and} \quad (17)$$

$$\vec{y_{t_{inWorld}}} = \begin{bmatrix} x_{s_1}d + y_{s_1}e + z_{s_1}f \\ x_{s_2}d + y_{s_2}e + z_{s_2}f \\ x_{s_3}d + y_{s_3}e + z_{s_3}f \end{bmatrix} \quad (18)$$

From the equations in the section entitled "Converting Cartesian Coordinates to Tilt Angles," it is known that:

$$x_3 = \sin\phi$$

$$z_3 = \sin\theta$$

$$y_3 = \sin\zeta$$

Therefore:

$$\phi_t = a\sin(x_{s_3}a + y_{s_3}b + z_{s_3}c) \quad (19)$$

$$\zeta_t = a \sin(x_{s_3} d + y_{s_3} e + z_{s_3} f) \quad (20)$$

$$\theta_t = a \sin(x_{s_3} g + y_{s_3} h + z_{s_3} j) \quad (21)$$

Replacing $x_{s_3}$, $y_{s_3}$ and $z_{s_3}$ by their representation in terms of the tilt angles of S, there is obtained:

$$\phi_t = \arcsin(\sin(\phi_s)a + \sin(\zeta_s)b + \sin(\theta_s)c) \quad (22)$$

$$\zeta_t = \arcsin(\sin(\phi_s)d + \sin(\zeta_s)e + \sin(\theta_s)f) \quad (23)$$

$$\theta_t = \arcsin(\sin(\phi_s)g + \sin(\zeta_s)h + \sin(\theta_s)j) \quad (22)$$

Therefore, using only the known relative orientation of T and S, and the current measures of sensor S, $\phi_s$, $\zeta_s$ and $\theta_s$, $\phi_t$, $\zeta_t$ and $\theta_t$ can be retrieved, that is the tilt angles of the virtual sensor T in the world coordinate system.

If the rigid 3D transformation between a tilt sensor and any point on a bone or instrument is known, the tilt angles of this point can be found as if a sensor were there.

The accelerometers can only give two out of the three degrees of freedom necessary to fully define the orientation. The third degree of freedom, the yaw, would require a compass.

However, if a controlled motion is applied on a pair of accelerometers, the tilt angles on the two accelerometers are obtained, and their relative yaw can be deduced from those readings.

Figure 6:
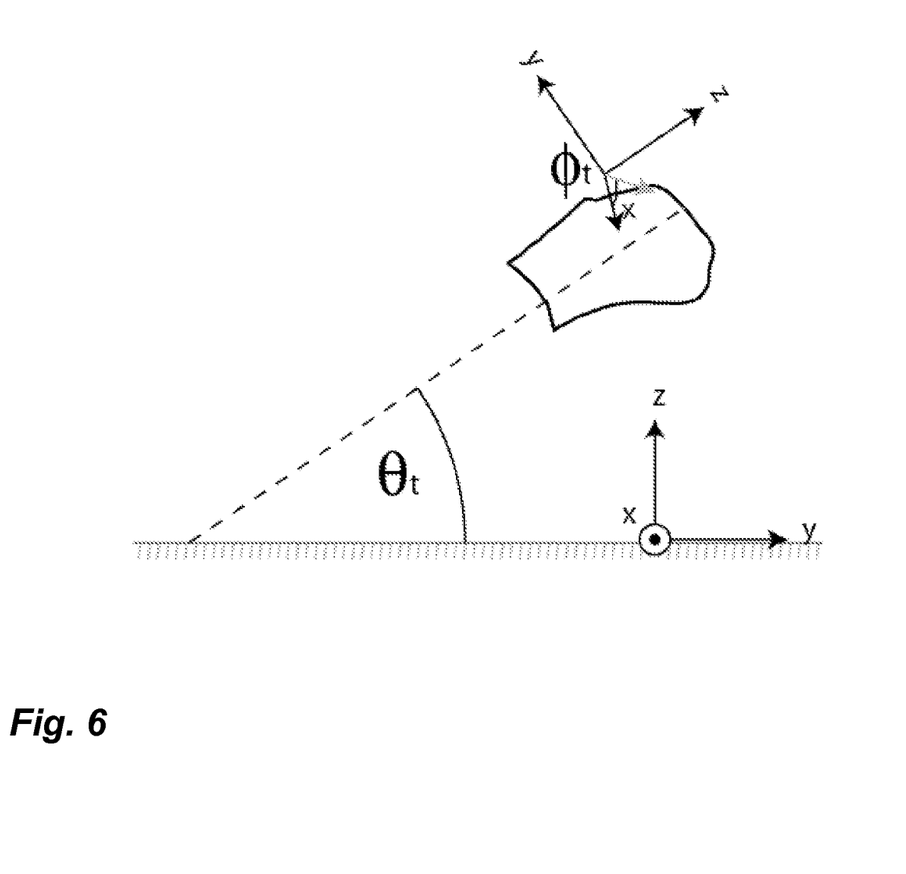
FIG. 6 is a schematic representation of sensors on a bone in accordance with a calibration method of the present disclosure.

With the set-up of FIG. 6, the tibial sensor T is perfectly aligned with the tibia axes. The operator places the tibia in extension, with the tibia mostly parallel to the ground ($\theta_t = 0$). In FIG. 6, the $\vec{y}$ axis of the world is aligned with the tibia by convention. The $\vec{x}$ axis of the tibia does not need to be parallel to the ground.

Another sensor B is placed arbitrarily on the tibia. The orientation of this sensor B in the world coordinate system is not known, but is defined as follows:

$$\begin{bmatrix} x_{b_1} & y_{b_1} & z_{b_1} \\ x_{b_2} & y_{b_2} & z_{b_2} \\ x_{b_3} & y_{b_3} & z_{b_3} \end{bmatrix}$$

This rotation can also be expressed in terms of the angles $\phi_b$, $\theta_b$, $\zeta_b$ and $\psi_b$, with the relationship between $R_B$ and those angles being defined by the equations in the previous section entitled "Converting Tilt Angles to Cartesian."

From sensor T, $\theta_t$ and $\phi_t$ (which will be between $-90°$ and $90°$) are obtained, while $\psi_t$ will always be zero. If the tibia rotates about the gravity vector, the world coordinate system will also rotate to respect this constraint. Accordingly, $T_{in\ world}$ may be calculated, namely, the full orientation of the tibia in the world coordinate system.

To avoid the need for a compass, it is assumed that the "north" of the coordinate system always follows the tibia. Because of this, there is no need to restrain the rotation of the tibia around the gravity vector.

From sensor B, $\theta_b$ can be measured, while $\phi b$, $\psi_b$ cannot be observed, and will be unknown. If this missing variable is found, the full relative orientation between the two sensors will be known.

The operator changes the orientation of the tibia. The actual orientation is irrelevant as long as it is sufficiently different from the previous one, and not strictly around the gravity vector.

Any large change in orientation would work with this algorithm. However, it might be suitable to guide the operator toward a precise orientation to facilitate the usability, or indicate to the operator that the indexed change in orientation is sufficient. It is recommended to use two acquisitions in flexion and extension.

By convention, $\psi'_t$ remains zero (i.e., the world coordinate system rotates about the gravity vector to follow the tibia). Thus, knowing $\theta'_t$ and $\phi'_t$, $T'_{in\ world}$, the orientation of the tibia after the transformation in the world coordinate system, can be calculated.

The same transformation also applies to sensor B, whose new rotation in the world coordinate system is $R'_B$, defined interchangeably in the form $(\phi'_b, \theta'_b, \psi'_b)$ or $(\vec{x}'_b, \vec{y}'_b, \vec{z}'_b)$ and $\theta'_B$ can be read directly from the accelerometer, but $\psi'_b$ remains unknown.

$T_{in\ world}$, $T'_{in\ world}$ and $R_B$ (i.e., B in the world) are combined to obtain an expression of $R'_B$ as a function of $R_B$.

$$sensorInTibia = worldInTibia \cdot sensorInWorld$$
$$= sensor'InTibid$$
$$= worldInTibid \cdot sensor'InWorld$$

$$worldInTibia \cdot sensorInWorld = worldInTibia' \cdot sensor'InWorld$$

$$T_{in\ world}^{-1} \cdot R_B = T'_{in\ world}{}^{-1} \cdot R'B$$

$$R'_B = T'_{in\ world} \cdot T_{in\ world}^{-1} \cdot R_B \quad (25)$$

Since $T_{in\ world}$ and $T'_{in\ world}$ are fully known, their combination is shown as matrix M.

$$M = T'_{in\ world} \cdot T_{in\ world}^{-1} \quad (26)$$
$$= \begin{bmatrix} m_{11} & m_{12} & m_{13} \\ m_{21} & m_{22} & m_{23} \\ m_{31} & m_{32} & m_{33} \end{bmatrix}$$

Equation (25) then becomes:

$$R'_B = M \cdot R_B \quad (27)$$

$$\begin{bmatrix} x'_{b_1} & y'_{b_1} & z'_{b_1} \\ x'_{b_2} & y'_{b_2} & z'_{b_2} \\ x'_{b_3} & y'_{b_3} & z'_{b_3} \end{bmatrix} = \begin{bmatrix} m_{11} & m_{12} & m_{13} \\ m_{21} & m_{22} & m_{23} \\ m_{31} & m_{32} & m_{33} \end{bmatrix} \cdot \begin{bmatrix} x_{b_1} & y_{b_1} & z_{b_1} \\ x_{b_2} & y_{b_2} & z_{b_2} \\ x_{b_3} & y_{b_3} & z_{b_3} \end{bmatrix}$$

From equations (6), (9) and (10), it is known that:

$$z_1 = -\cos\theta \sin\psi$$

$$z_2 = -\cos\psi \sin\theta$$

$$z_3 = \sin\theta$$

Therefore:

$$\sin\theta'_b = z'_{b_3}$$

$$= m_{31} z_{b_1} + m_{32} z_{b_2} + m_{33} z_{b_3}$$

$$= -m_{31} \cos\theta_b \sin\psi_b + m_{32} \cos\psi_b \cos\theta_b + m_{33} \sin\theta_b \quad (28)$$

Then, $\psi_b$ is isolated in the previous equation to find the following:

$$\psi_b = \pm \arccos\left(\frac{m_{32}\sec(\theta_b)\sin(\theta_b') - m_{32}m_{33}\tan(\theta_b) \pm \sec^2(\theta_b)\sqrt{u}}{m_{31}^2 + m_{32}^2}\right) \quad (29)$$

where:

$$u = m_{31}^2 \cos^2(\theta_b)((m_{31}^2 + m_{32}^2)\cos^2(\theta_b) - (\sin(\theta_b') - m_{33}\sin(\theta_b))^2) \quad (30)$$

This gives four potential solutions, corresponding to the four combinations of ± in the equation. One cannot directly distinguish between all four solutions by looking at $\phi_b$ and $\theta_b$.

However, four possible matrices ($R_{bi}$) can be formed corresponding to ($\phi_b$, $\theta_b$, $\psi_{b_1}$), ($\phi_b$, $\theta_b$, $\psi_{b_2}$), ($\phi_b$, $\theta_b$, $\psi_{b_3}$) and ($\phi_b$, $\theta_b$, $\psi_{b_4}$). Transformation M is then applied to all four solutions to obtain the expected $R'_{bi}$, and the resulting $\phi'_{bi}$ is obtained as follows:

$$\phi'_{bi} = a\sin(x'_{bi_3}) \quad (31)$$
$$= a\sin(m_{31} * x_{bi_1} + m_{32} * x_{bi_2} + m_{33} * x_{bi_3}))$$

The only one of the four candidate solutions that will yield the correct $\phi'_{bi}$ is thus identified.

Some sensor configurations are more suitable than others for optimal accuracy. For instance, the reference should not be aligned too closely with the tibia in case of TKR.

Among suitable configurations are a few configurations where the sensor axes are perpendicular to the tibia axes, but rotated by increments of 90° (e.g., tibia$_{in\ sensor}$=(0, $\sqrt{0.5}$, 0, $\sqrt{0.5}$) and tibia$_{in\ sensor}$=($\sqrt{0.5}$, 0, $-\sqrt{0.5}$,0)). Other suitable configurations are considered as well.

It may not be convenient for mechanical purposes to place the reference in a specified optimal location. It is possible to apply a virtual transformation to the reference using the algorithms of the previous section entitled "Navigation of a Virtual Sensor Relative to a Reference," and to find the relative position of this virtual reference to the tibia. The inverse of the virtual transformation is then applied to retrieve the relative position of the real reference to the tibia.

The complete algorithm is then as follows:
  Given two sets of tilt angles for the bone, the relative transformation between those two orientations is calculated, assuming a yaw of zero in both cases.
  Given two sets of tilt angles for the reference, a known transformation T is applied to both sets to calculate the tilt angles of a virtual reference [using equation (24)].
  Equation (29) is applied to the virtual reference tilt angles to retrieve the relative orientation of the virtual reference relative to the bone.
  The inverse of T is reapplied to retrieve the relative orientation of the real reference relative to the bone. The calibration has, therefore, enabled the calculation of a third DOF in orientation.

Figure 7:
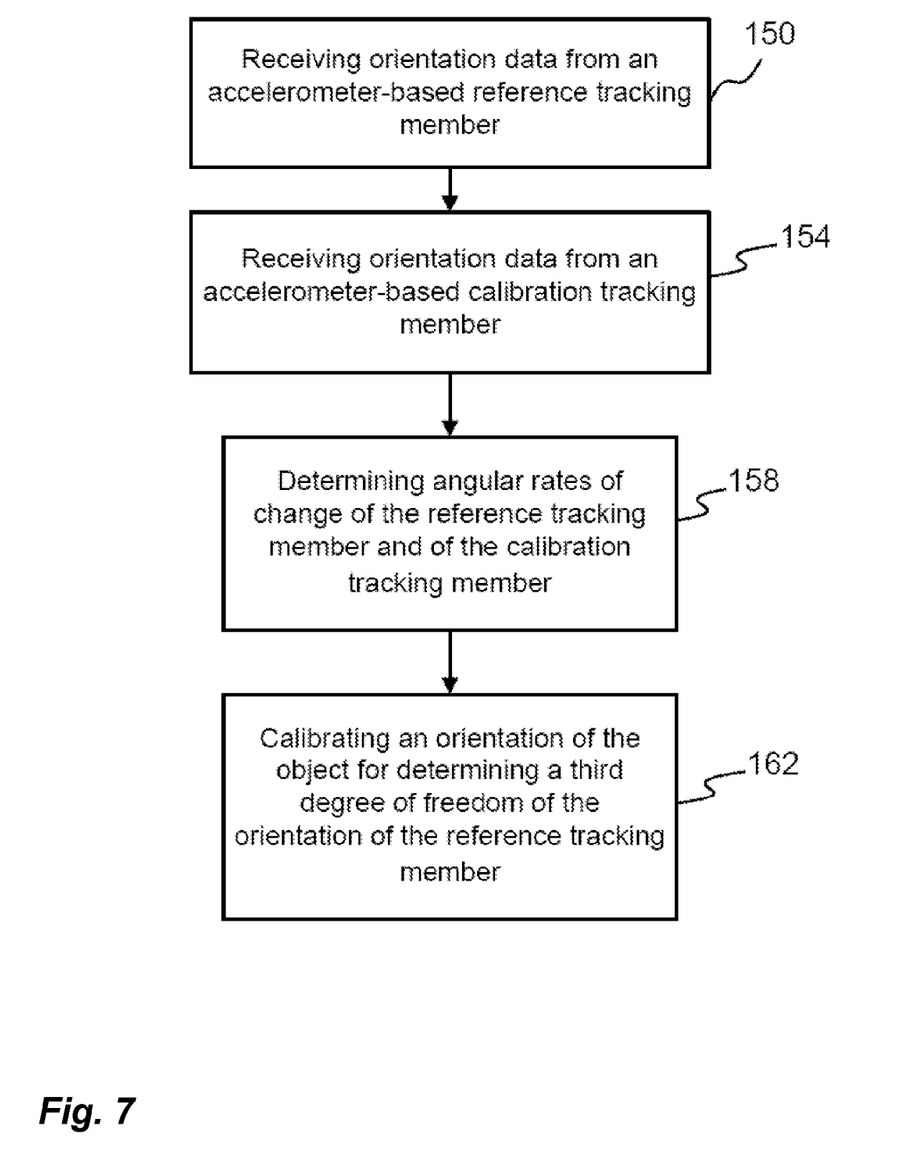
FIG. 7 is a flowchart illustrating a method for tracking three degrees of freedom of orientation of an object using the tracking system of FIGS. 3 and 4.

Therefore, further to the above-described steps, referring to FIG. 7, a method is provided to calibrate a trackable member 12/12' having an accelerometer providing orientation data for 2 DOFs in orientation, so as to provide a $3^{rd}$ DOF for the trackable member 12/12'.

As shown in FIGS. 2-4, the method comprises providing two of the trackable members 12/12' having accelerometers, and mounting both trackable members 12/12' to the tracked element 10. One of the trackable members 12/12' is the reference tracking member, another is a calibration tracking member. Accordingly, the trackable members 12/12' both produce 2-DOF orientation data pertaining to the object.

Referring again to FIG. 7 and according to 150 and 154, the orientation data from both trackable members 12/12' is received by the processing unit of the tracking system 100. The operator then performs motions of the object.

According to 158, the processing unit of the tracking system 100 determines the angular rates of change of the reference tracking member 12/12' and of the calibration tracking member 12/12' while the object moves. Reference to the angular rates of change hereinafter pertains to a change in relative angle/yaw.

With these angular changes, the processing unit of the tracking system 100 can determine the $3^{rd}$ DOF of the reference tracking member 12/12', as set forth above. Accordingly, at 162, the processing unit of the tracking system 100 calibrates an orientation of the object with reference to the reference tracking member 12/12' by using the determined angular rates of change, to determine the $3^{rd}$ degree of freedom of orientation of the reference tracking member 12/12'. With this calibration procedure, the tracked element 10 is trackable in three degrees of freedom of orientation through the tracking data provided by the reference tracking member 12/12'.

The method involves defining a local coordinate system aligned with the gravity vector and one of the axes of the reference tracking member 12/12', and constraining the $3^{rd}$ degree of freedom of the reference tracking member 12/12'. The orientation of the reference tracking member 12/12' and the calibration tracking member 12/12' can be expressed in this local coordinate system, before and after the movement of the object mentioned above.

For the method of FIG. 7, it is exemplary to perform movements of greater amplitude for the object at 158, as the movements will result in greater values of angular rates of change. With greater angular rates of change, more precision may be attained in calibrating the $3^{rd}$ DOF.

The invention claimed is:

1. A computer-assisted surgery system for tracking an instrument and a bone during surgery, comprising:
  a first trackable member having a first inertial sensor unit producing at least orientation-based data, the first inertial sensor unit being an accelerometer-based unit adapted to be affixed to the bone, to produce orientation data for two degrees of freedom of orientation; and
  a second trackable member having a second inertial sensor unit producing at least orientation-based data, the second inertial sensor unit being an accelerometer-based unit adapted to be affixed to the bone, to produce orientation data for two degrees of freedom of orientation; and
  a processing unit for receiving the orientation-based data from the trackable members, the processing unit comprising:
    an orientation calculator calculating an orientation of the second trackable member with respect to the first trackable member from the orientation-based data of the trackable members, the orientation calculator determining angular rates of change of the first inertial sensor unit and the second inertial sensor unit while the bone is moved in space in at least two degrees of freedom, and
    a calibration calculator for calibrating an orientation of the bone with reference to the first inertial sensor unit by using the determined angular rates of change to determine a third degree of freedom of orientation of the first inertial sensor unit,
  whereby the bone is trackable in three degrees of freedom of orientation.

2. The computer-assisted surgery system according to claim 1, wherein the first trackable member and the second trackable member produce position-based data, and the processing unit stores geometrical data relating at least one of the trackable members to the bone and another of the trackable members to the instrument, whereby the orientation calculator calculates a position and orientation of the instrument with respect to the bone.

3. The computer-assisted surgery system according to claim 1, wherein the processing unit is physically part of the second trackable member.

4. The computer-assisted surgery system according to claim 3, wherein the second trackable member has a user interface to display the orientation of the second trackable member with respect to the first trackable member.

5. The computer-assisted surgery system according to claim 1, wherein at least one of the trackable members has a confirmation indicator receiving signals from the processing unit to visually display a confirmation of command from the at least one trackable member.

6. The computer-assisted surgery system according to claim 1, wherein the first trackable member and the second trackable member are arbitrarily placed on the bone, and the processing unit determines a preferred virtual orientation from the orientation of the second trackable member with respect to the first trackable member, the orientation calculator determining the angular rates of change from the preferred virtual orientation.

7. A method for tracking three degrees of freedom of orientation of an object, the method comprising:
receiving orientation data for two degrees of freedom of orientation from an accelerometer-based reference tracking member affixed to the object;
receiving orientation data for two degrees of freedom of orientation from an accelerometer-based calibration tracking member affixed to the object;
determining angular rates of change of the reference tracking member and of the calibration tracking member while the object is moved in space in at least two degrees of freedom; and
calibrating an orientation of the object with reference to the reference tracking member by using the determined angular rates of change to determine a third degree of freedom of orientation of the reference tracking member;
whereby the object is trackable in three degrees of freedom of orientation.

8. The method according to claim 7, wherein receiving orientation data comprises receiving orientation data from the reference and calibration tracking members affixed to a bone.

9. The method according to claim 7, wherein determining angular rates of change of the reference tracking member and of the calibration tracking member comprises displaying data associated to an angular rate of change, for guiding an operator in moving the object.

10. The method according to claim 7, further comprising performing the method with a bone model or a cadaver.

11. The method according to claim 7, further comprising displaying a tracking of the object in three degrees of freedom of orientation on an interface after the calibrating.

12. The method according to claim 7, wherein receiving orientation data from the reference tracking member comprises first placing the reference tracking member in alignment with object axes.

13. The method according to claim 7, wherein receiving orientation data from the reference tracking member comprises randomly placing the reference tracking member on the object, and determining a preferred orientation of the reference tracking member with respect to the object, and further wherein determining angular rates of change comprises determining angular rates of change relative to the preferred orientation of the reference tracking member.

14. A system for tracking three degrees of freedom of an orientation of an object, the system comprising:
an accelerometer-based reference tracking member adapted to be affixed to the object, the reference tracking member producing orientation data for two degrees of freedom of orientation;
an accelerometer-based calibration tracking member adapted to be affixed to the object, the calibration tracking member producing orientation data for two degrees of freedom of orientation;
a processing unit for receiving the orientation data from the reference tracking member and the calibration tracking member, the processing unit comprising:
an orientation calculator for determining angular rates of change of the reference tracking member and the calibration tracking member while the object is moved in space in at least two degrees of freedom; and
a calibration calculator for calibrating an orientation of the object with reference to the reference tracking member by using the determined angular rates of change to determine a third degree of freedom of orientation of the reference tracking member;
whereby the object is trackable in three degrees of freedom of orientation.

15. The system according to claim 14, wherein the system is a computer-assisted surgery system, the object is a bone and the reference tracking member and the calibration tracking member are affixed to the bone.

16. The system according to claim 14, further comprising a user interface for displaying data associated with an angular rate of change about the axis of one of the two degrees of freedom of orientation of the reference tracking member, for guiding an operator in moving the object.

17. The system according to claim 16, wherein the user interfaces displays a tracking of the object in three degrees of freedom of orientation on an interface after the calibrating.

18. The system according to claim 14, wherein the reference tracking member and the calibration tracking member are randomly placed on the object, and the processing unit determines a preferred orientation of the reference tracking member with respect to the object, the orientation calculator further determining the angular rates of change from the preferred orientation.

19. The computer-assisted surgery system according to claim 1, wherein the orientation calculator determines angular rates of change of the first inertial sensor unit and the second inertial sensor unit while the bone is moved in space unconstrained to a single degree of freedom.

20. The method according to claim 7, wherein determining angular rates of change of the reference tracking member and of the calibration tracking member determining angular rates of change of the reference tracking member and of the calibration tracking member while the object is moved in space unconstrained to a single degree of freedom.

21. The system according to claim 14, wherein the orientation calculator determines angular rates of change of the first inertial sensor unit and the second inertial sensor unit while the bone is moved in space unconstrained to a single degree of freedom.

* * * * *